(12) United States Patent
Specht et al.

(10) Patent No.: US 8,487,210 B2
(45) Date of Patent: Jul. 16, 2013

(54) JOINED DISSIMILAR MATERIALS AND METHOD

(75) Inventors: Heiko Specht, Hanau (DE); Andreas Reisinger, Alzenau (DE); Goran Pavlovic, Schaafheim (DE); Jacob Markham, Vadnais Heights, MN (US); Kelly Stichter, Stillwater, MN (US); Laurent Bataillard, Vaud (CH)

(73) Assignee: W. C. Hereaus GmbH, Hanau (DE)

( * ) Notice: Subject to any disclaimer, the term of this patent is extended or adjusted under 35 U.S.C. 154(b) by 261 days.

(21) Appl. No.: 12/813,847

(22) Filed: Jun. 11, 2010

(65) Prior Publication Data

US 2011/0306949 A1    Dec. 15, 2011

(51) Int. Cl.
*B23K 26/00* (2006.01)
(52) U.S. Cl.
USPC ....... 219/121.64; 313/631; 600/585; 604/528
(58) Field of Classification Search
USPC ....... 313/631; 600/585; 604/528; 219/121.64
See application file for complete search history.

(56) References Cited

U.S. PATENT DOCUMENTS

| | | | |
|---|---|---|---|
| 2,367,206 A | 1/1945 | Davis | |
| 3,314,583 A | 4/1967 | Roberts | |
| 3,612,386 A | 10/1971 | Gibson et al. | |
| 3,691,622 A | 9/1972 | Takagi et al. | |
| 3,769,685 A | 11/1973 | Noda | |
| 3,897,896 A | 8/1975 | Louw et al. | |
| 4,811,887 A | 3/1989 | King et al. | |
| 5,368,661 A | 11/1994 | Nakamura et al. | |
| 5,714,103 A | 2/1998 | Bauer et al. | |
| 6,036,725 A | 3/2000 | Avellanet | |
| 6,637,642 B1 | 10/2003 | Lingnau | |
| 6,645,159 B1 | 11/2003 | Burkett | |
| 6,648,206 B2 | 11/2003 | Nelson et al. | |
| 6,779,704 B2 | 8/2004 | Nelson et al. | |
| 6,875,949 B2 | 4/2005 | Hall | |
| 6,877,277 B2 * | 4/2005 | Kussel et al. | 49/314 |
| 6,918,882 B2 | 7/2005 | Skujins et al. | |

(Continued)

FOREIGN PATENT DOCUMENTS

| | | |
|---|---|---|
| EP | 0321796 | 6/1989 |
| EP | 0566523 | 10/1993 |

(Continued)

OTHER PUBLICATIONS

Andersen, Olaf, et al, "Direct Typing—A New Method for the Production of Cellular P/M Parts," Proceedings, Euro PM, Vol, 4, pp. 1-6 (2004).

(Continued)

*Primary Examiner* — Tan N Tran
(74) *Attorney, Agent, or Firm* — Dicke, Billig & Czaja, PLLC

(57) ABSTRACT

A wire includes a first wire section is of a first material and a second wire section is of a second material different from the first material. A joining section is adjacent both the first and second wire sections, the joining section comprising a first end and a second end. The first end of the joining section is of a material that is compatible with the first material of the first wire section and the second end of the joining section is of a material that is compatible with the second material of the second wire section.

12 Claims, 5 Drawing Sheets

U.S. PATENT DOCUMENTS

| | | |
|---|---|---|
| 7,074,197 B2 * | 7/2006 | Reynolds et al. ............. 600/585 |
| 7,124,929 B2 | 10/2006 | Nelson et al. |
| 7,152,776 B2 | 12/2006 | Nelson et al. |
| 7,270,257 B2 | 9/2007 | Steel et al. |
| 7,277,762 B2 | 10/2007 | Belden et al. |
| 7,632,237 B2 | 12/2009 | Murayama et al. |
| 2004/0039310 A1 | 2/2004 | Burkett |
| 2004/0167443 A1 | 8/2004 | Shireman et al. |
| 2005/0035173 A1 | 2/2005 | Steel et al. |
| 2005/0116012 A1 | 6/2005 | Packer et al. |
| 2005/0256563 A1 | 11/2005 | Clerc et al. |
| 2006/0047223 A1 | 3/2006 | Grandfield et al. |
| 2006/0122537 A1 | 6/2006 | Reynolds et al. |
| 2006/0204919 A1 | 9/2006 | Thiry |
| 2006/0237407 A1 | 10/2006 | Nguyen et al. |
| 2008/0009934 A1 | 1/2008 | Schneider et al. |
| 2008/0154152 A1 | 6/2008 | Satou et al. |
| 2008/0217055 A1 | 9/2008 | Gumley |
| 2011/0147080 A1 | 6/2011 | Slininger et al. |

FOREIGN PATENT DOCUMENTS

| | | |
|---|---|---|
| EP | 0515201 | 9/1997 |
| EP | 1178867 | 9/2004 |
| EP | 1432467 | 12/2005 |
| JP | 2000042744 | 2/2000 |
| JP | 2003159333 | 6/2003 |
| WO | 9519800 | 7/1995 |
| WO | 9919017 | 4/1999 |
| WO | 0025973 | 5/2000 |
| WO | 0145578 | 6/2001 |
| WO | 0185385 | 11/2001 |
| WO | 03030982 | 4/2003 |
| WO | 2005053890 | 6/2005 |
| WO | 2006025931 | 3/2006 |
| WO | 2008014849 | 2/2008 |

OTHER PUBLICATIONS

Cohen, Adam L., "EFAB® Technology: Unlocking the Potential of Miniaturized Medical Devices," Microfabrica Inc., pp. 1-31 (2008).

Forschungszentrum Karlsruhe GmbH, "The LIGA-Process (An outline)," Key Technologies, Microsystem Technologies, Fabrication Technologies • Materials, pp. 2 (Sep. 10, 2005). (English Version. pp. 2).

Leonard, Shana, "Welding Technnlogy Fuses Nitinol to Stainless Steel," Medical Device Link (originally published EMDM), pp, 2 (May/Jun. 2007).

Office Action for U.S. Appl. No. 12/644,818 mailed Mar. 15, 2012 (22 pages).

* cited by examiner

| | 20 | 21 | 22 | 23 | 24 | 25 | 26 | 27 | 28 | 29 | 30 |
|---|---|---|---|---|---|---|---|---|---|---|---|
| STAINLESS STEEL | 100 | 90 | 80 | 70 | 60 | 50 | 40 | 30 | 20 | 10 | 0 |
| NICKEL-TITANIUM | 0 | 10 | 20 | 30 | 40 | 50 | 60 | 70 | 80 | 90 | 100 |

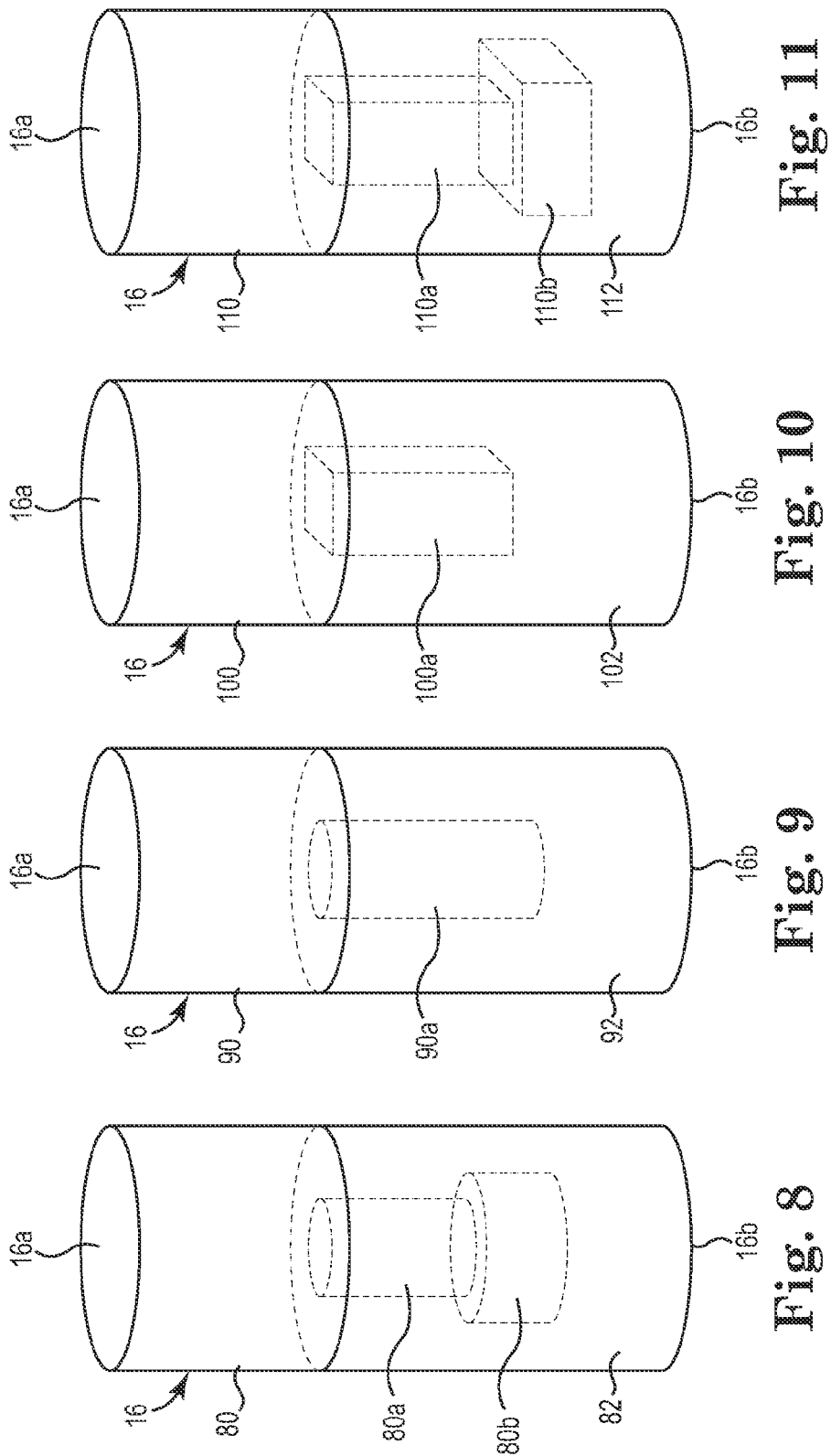

1

JOINED DISSIMILAR MATERIALS AND METHOD

BACKGROUND

The present invention relates to joined dissimilar materials. In one embodiment, the joined materials form a guide wire configured for intravascular use. For example, intravascular guidewires are used in conjunction with intravascular devices such as catheters to facilitate navigation through the vasculature of a patient. Such guidewires are typically very small in diameter. In some applications, a guidewire can have multiple sections that are joined together in order to form a single wire. Joining sections of such a wire having a small diameter can be challenging, particularly where the sections being joined are configured of different materials. Because there are limitations to many present approaches, there is a need for the present invention.

BRIEF DESCRIPTION OF THE DRAWINGS

FIG. 8 illustrates a perspective partially ghosted view of a joining section in accordance with one embodiment.

FIG. 9 illustrates a perspective partially ghosted view of a joining section in accordance with one embodiment.

FIG. 10 illustrates a perspective partially ghosted view of a joining section in accordance with one embodiment.

FIG. 11 illustrates a perspective partially ghosted view of a joining section in accordance with one embodiment.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1A:
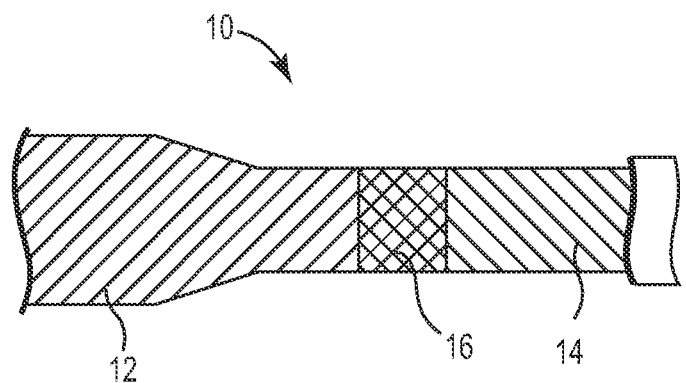
FIGS. 1A and 1B illustrate cross-sectional views of joined dissimilar materials in accordance with one embodiment.

FIG. 1A illustrates a guidewire 10 in accordance with one embodiment. In one embodiment, guidewire 10 has a proximal section 12, a distal section 14 and a joining section 16. In one case, proximal, distal and joining sections 12, 14 and 16 are each configured of separate wire segments that are joined together at joining section 16. In some embodiments, proximal and distal sections 12 and 14 are adapted with differing diameter regions, are adapted and configured to obtain a transition in stiffness, and provide a desired flexibility characteristic. In FIG. 1, guidewire 10 is illustrated with a truncation in its ends, as its length may vary in accordance with particular applications.

As used herein, the proximal section 12 and the distal section 14 can generically refer to any two adjacent wire sections along any portion of guidewire 10. Furthermore, although discussed with specific reference to guidewires, the wire segments can be applicable to almost any intravascular device. For example, they are applicable to hypotube shafts for intravascular catheters (e.g., rapid exchange balloon catheters, stent delivery catheters, etc.) or drive shafts for intravascular rotational devices (atherectomy catheters, IVUS catheters, etc.).

In one example, proximal section 12 can be configured of a relatively stiff material, such as stainless steel wire. Alternatively, proximal section 12 can be comprised of a metal or metal alloy such as a nickel-titanium alloy, nickel-chromium alloy, nickel-chromium-iron alloy, cobalt alloy, or other suitable material. In general, the material used to construct proximal section 12 can be selected to be relatively stiff for pushability and torqueability.

Also, in some embodiments, distal section 14 can be configured of a relatively flexible material, such as a super elastic or linear elastic alloy, wire, such as linear elastic nickel-titanium (NiTi), or alternatively, a polymer material, such as a high performance polymer. Alternatively, distal section 14 can be configured of a metal or metal alloy such as stainless steel, nickel-chromium alloy, nickel-chromium-iron alloy, cobalt alloy, or other suitable material. In general, the material used to configure distal section 14 can be selected to be relatively flexible for trackability.

In one embodiment, guidewire 10 is configured for intravascular use and can be used in conjunction with intravascular devices such as catheters to facilitate navigation through the vasculature of a patient. Guidewire 10 is configured in a variety of sizes, and in one embodiment, its outer diameter ranges from about 0.005 to about 0.02 inches.

Figure 1B:
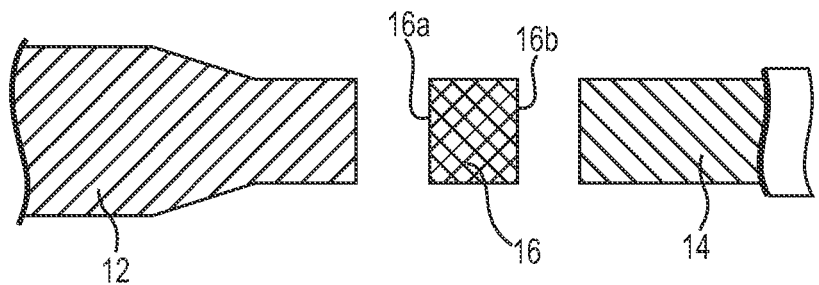

FIG. 1B illustrates an exploded view of guidewire 10 in accordance with one embodiment. Joining section 16 is made of two different materials. For example, on a first end 16a directly adjacent proximal section 12, joining section 16 is made of a material that is compatible with the material of which proximal section 12 is made. As such, proximal section 12 can be readily and easily welded to first end 16a of joining section 16, because of the compatible materials. Furthermore, on a second end 16b directly adjacent distal section 14, joining section 16 is made of a material that is compatible with the material of which distal section 14 is made. As such, distal section 14 can be readily and easily welded to second end 16b of joining section 16, because of the compatible materials.

In one embodiment, first end 16a of joining section 16 is stainless steel and proximal section 12 is also stainless steel. Also, second end 16b of joining section 16 is nickel-titanium (NiTi) and distal section 14 is also nickel-titanium. In this way, first end 16a is readily weldable to proximal section 12 and second end 16b is readily weldable to distal section 14.

In one embodiment, first end 16a of joining section 16 is a metal or metal alloy such as nickel-chromium alloy, nickel-chromium-iron alloy, cobalt alloy, or other similar material and proximal section 12 is of a highly similar material. Also, second end 16b of joining section 16 is made of a relatively flexible material, such as a super elastic or linear elastic alloy, and distal section 14 is of a highly similar material. In this way, first end 16a is readily weldable to proximal section 12 and second end 16b is readily weldable to distal section 14. Forming joining section 16, which is made of two different materials, can be accomplished in a variety of ways consistent with the exemplary embodiments.

Figures 2, 3:
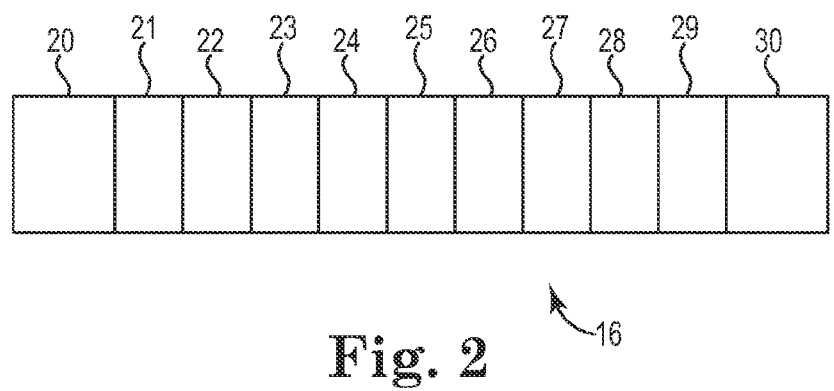
FIG. 2 illustrates a cross-sectional view of a joining section in accordance with one embodiment.
FIG. 3 is a table illustrating the material content of layers of a joining section in accordance with one embodiment.

FIG. 2 illustrates one embodiment of joining section 16 formed via layer sections. In one embodiment, joining section 16 consists of a plurality of layer sections, in one example, layers 20-30. In one embodiment, the material in each of the layers 20-30 varies from one layer to the next. For example, in one example, layer 20 of joining section 16 is all stainless steel, layer 21 is mostly stainless steel, but also includes a small amount of nickel-titanium. Each of layers 22-29 then progressively includes increasing amounts of nickel-titanium and decreasing amounts of stainless steel. Layer 30 is all nickel-titanium. As such, layer 20 is readily weldable to stainless steel proximal section 12 and layer 30 is readily weldable to a nickel-titanium distal section 14.

FIG. 3 illustrates the material content, as a percentage, for each of the layers of joining section 16 in one example. As such, layer 20 is 100% stainless steel and 0% nickel-titanium, layer 21 is 90% stainless steel and 10% nickel-titanium, layer 22 is 80% stainless steel and 20% nickel-titanium, layer 23 is 70% stainless steel and 30% nickel-titanium, and so forth, until layer 30, which is 0% stainless steel and 100% nickel-titanium.

In other embodiments, more or less layers can be used in order to more gradually or more steeply change the material content of joining section 16 from one of its end to the other. In the illustration, 11 layers are shown, but more or fewer layers can be used in accordance with various embodiments. Also, various other percentages of material changes can be used. In the illustrations, the percentages of material changes from one layer to the next are shown in increments of 10, but larger or smaller increments can be used in accordance with various embodiments.

In one embodiment, the layer sections of joining section 16 are formed via three-dimensional screen printing or Direct Typing Process (DTP). Three-dimensional screen printing, or DTP, is a known process for producing three-dimensionally shaped objects via a layering process. DTP uses to form a green compact by printing a liquefied metallic powder composition onto a substrate, and then repeating layer by layer until the green compact is obtained and the compact is sintered to a metal.

In one embodiment, a green compact is formed in order to make joining section 16. Initially, a metal-containing paste is mixed and then pressed through a sieve or mask. In one embodiment, the paste also contains an organic binder and a carrier liquid, for example, water. A first layer, such as layer 20, is printed by pushing the paste through a screen with a first print. In the first screen print, the metal-containing paste includes a first metal material and includes none of a second metal material. The first layer is then allowed to dry. A second layer is then printed on the first dried layer. Between the printing of the first and second layers, however, the composition of the paste is varied such that the amount of the first metal material is reduced and the amount of the second metal material is increased from none.

Each subsequent layer is then printed over the dried previous layer, gradually adjusting the composition of the metal-containing paste between each printing such that a gradient progressing from the first metal material to the second metal material is produced in the green compact. Subsequently, the green compact is debindered and sintered, whereby a joining section, such as joining section 16 of FIG. 2, is obtained.

In one embodiment, the individual printed layers of the green compact are on the order of 10-40 μm. As such, in one example, two or more layers may be printed before the composition of the paste is varied. In this way, a gradient progressing from the first metal material to the second metal material is still produced in the green compact, but each layer illustrated in FIG. 2 may actually represent two or more actual printed layers.

In one embodiment, the first material in the above-described three-dimensional screen printing or DTP is stainless steel and the second material is nickel-titanium. In another embodiment, first material is nickel-titanium and the second material is stainless steel. In other embodiments, still other materials can be used so that each end of the joining section 16 has a material composition that is compatible with the adjoining piece to which it will be connected or welded.

Figure 4:
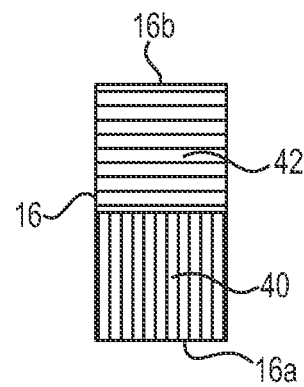
FIG. 4 illustrates a cross-sectional view of a joining section in accordance with one embodiment.

FIG. 4 illustrates one embodiment of joining section 16 formed via an electroplating or electrodeposition process. In one embodiment, joining section 16 includes a first section 40 and a second section 42, such that first end 16a of joining section 16 is on first section 40 and second end 16b of joining section 16 is on second section 42. Each of sections 40 and 42 are of different materials, and in one example, first section 40 is stainless steel and second section 42 is nickel-titanium (NiTi). In this way, first end 16a is readily weldable to proximal section 12 and second end 16b is readily weldable to distal section 14, as in FIG. 1A.

In one embodiment, first section 40 is metal, such as metal alloy, stainless steel, nickel, iron, nickel-chromium alloy, nickel-chromium-iron alloy, cobalt alloy, or other similar material and proximal section 12 is of a similar material. Also in one embodiment, second section 42 is made of a relatively flexible material, such as a super elastic or linear elastic alloy, and distal section 14 is of a similar material. In this way, first end 16a of first section 40 is readily weldable to proximal section 12 and second end 16b of second section 42 is readily weldable to distal section 14.

Figure 5A:
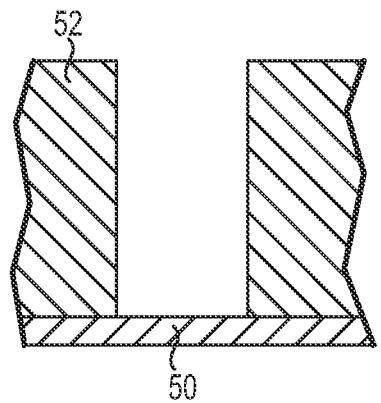
FIGS. 5A-5C illustrate forming a joining section in accordance with one embodiment.
Figure 5B:
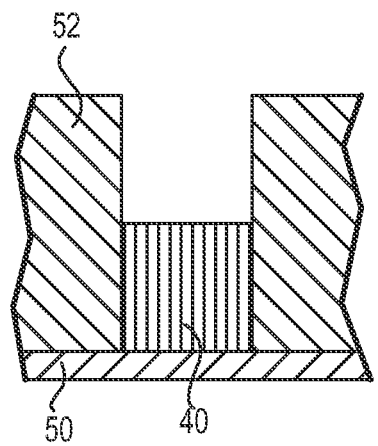
Figure 5C:
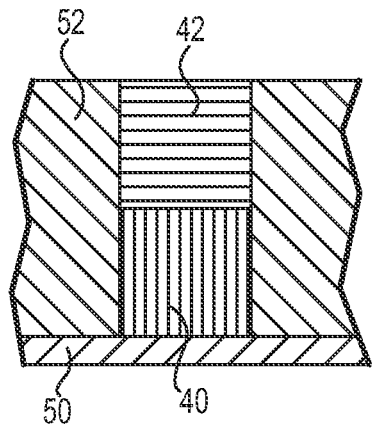

FIGS. 5A-5C illustrate one embodiment of a process for electrodeposition of joining section 16. In FIG. 5A, a mask 52 is deposited on a conductive substrate 50. Mask 52 defines an opening above conductive substrate 50 that is shaped to match the profile desired for joining section 16, in one example, cylindrical.

FIG. 5B illustrates an electrodeposition process whereby first section 40 is formed within the opening of mask 52 by energizing conductive substrate 50. In one example, the deposition of first section 40 is achieved by putting a negative charge on conductive substrate 50 and immersing conductive substrate 50 and mask 52 into a first electrolyte solution that contains a salt of the metal to be deposited as first section 40. In other words, conductive substrate 50 is made the cathode of an electrolytic cell. The metallic ions of the salt carry a positive charge and are thus attracted to conductive substrate 50. When they reach the negatively charged conductive substrate 50, it provides electrons to reduce the positively charged ions to metallic form.

In one embodiment, when first section 40 is metal, such as metal alloy, stainless steel, nickel, iron, nickel-chromium alloy, nickel-chromium-iron alloy, cobalt alloy, or other similar material, one of these materials is dissolved in the electrolytic solution as positively charged ions.

FIG. 5C illustrates formation of second section 42, which is built up on first section 40. Ions of the material that make up second section 42 are then contained within a second electrolytic solution in which mask 52 and conductive substrate 50 are submerged, and when conductive substrate 50 is energized, second section 42 is formed within mask 52 against first section 40 under the force of the energized conductive substrate 50.

In one embodiment, when section 42 is relatively flexible material, such as nickel-titanium (NiTi) or a super elastic or linear elastic alloy, one of these materials is dissolved in the electrolytic solution as positively charged ions.

In another embodiment, first section 40 can be formed by other means and then placed within mask 52 on conductive substrate 50. Then, second section 42 can be formed over first section 42 within mask 52 with an electrodeposition process using conductive substrate 50 as described above.

Figure 6:
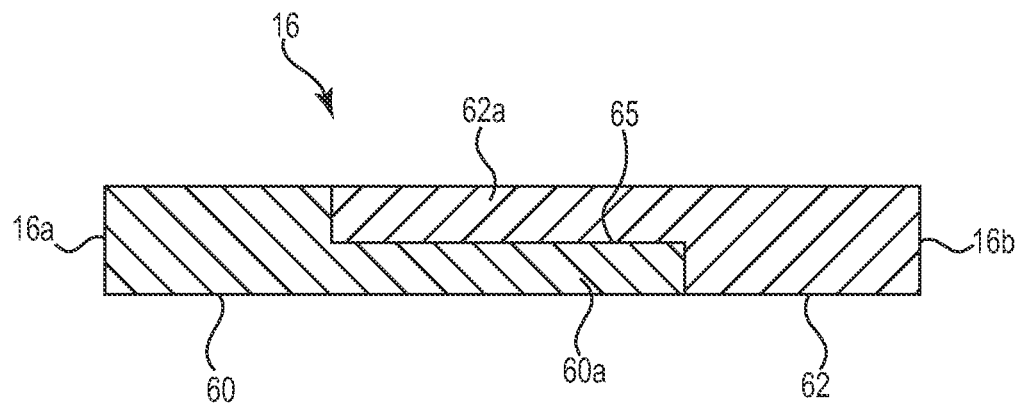
FIG. 6 illustrates a cross-sectional view of a joining section in accordance with one embodiment.
Figure 7:
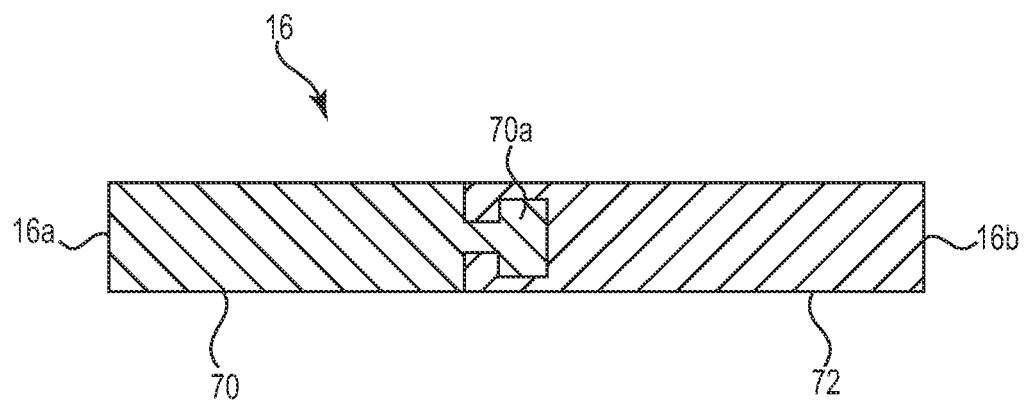
FIG. 7 illustrates a cross-sectional view of a joining section in accordance with one embodiment.

FIGS. 6 and 7 illustrate other embodiments of joining section 16 formed with an electrodeposition process. In one example, joining section 16 includes first section 60 and second section 62. First and second sections 60 and 62 are formed with an electrodeposition process as explained above. A conductive substrate 50 and mask corresponding to the shape of first and second sections 60 and 62 are used to electrode deposit one or both of first and second sections 60 and 62.

In one embodiment, first section 60 includes first extended portion 60a and second section 62 includes second extended portion 62a, which overlap along joint 65. As with above-described embodiments, either first or second section 60 or 62 can be electroplated first (or otherwise formed) and then the other section is electroplated on to the already formed section. Joint 65 is perpendicular to first and second ends 16a and 16b of joining section 16. In one example, having a feature such as joint 65 running perpendicular to ends 16a and 16b can provide increased holding force between first and second section 60 and 62 when there is significant pulling or torque applied to proximal section 12 and distal section 14, which are respectively coupled to ends 16a and 16b.

In one example, joining section 16 includes first section 70 and second section 72. First and second sections 70 and 72 are formed with an electrodeposition process as explained above. A conductive substrate 50 and mask corresponding to the shape of first and second sections 70 and 72 are used to electrodeposit one or both of first and second sections 70 and 72.

In one embodiment, first section 70 includes plug portion 70a and second section 72 is configured to receive plug portion 70a. As with above-described embodiments, either first or second section 70 or 72 can be electroplated first (or otherwise formed) and then the other section is electroplated on to the already formed section. In one example, having a features such as plug 70a formed within a receiving cavity of second section 72 can provide increased holding force between first and second section 70 and 72 when there is significant pulling or torque applied to proximal section 12 and distal section 14, which are respectively coupled to ends 16a and 16b.

Other configurations of joining section 16 are also possible in accordance with other embodiments and other electro-forming methods. In one embodiment, joining section 16 may be fabricated using LIGA or lithography and electroforming techniques. In one case, the LIGA process includes X-ray deep lithography, electroforming and molding.

In X-ray deep lithography, a polymer layer (resist) sensitive X-radiation is exposed to X-radiation by the shadow produced by an X-ray mask, which transfers to the resist an exact image of the absorber structures on the mask. The exposed areas are dissolved selectively by wet chemical methods. Somewhat complex or intricate configurations are possible using lithography techniques. When these polymer structures are produced on a metal starting layer, the structural areas exposed after the developing process can be filled up with various metals by electrodeposition. Once the metal is built up, the remaining resist is removed, and only the metal structures remain in place.

In other embodiments, EFAB® technology is used to create joining section 16. EFAB® technology is a known process for forming micro-structures by stacking a set of thin metal layers, somewhat similar to rapid prototyping technologies. The EFAB® process is driven by a three-dimensional CAD of the final device. The manufacturing starts with a blank substrate and then grows the device layer-by-layer by depositing and precisely planerizing metals. In one example, two metals are deposited (for example, one for the first section and one for the second section of a joining section). Somewhat complex or intricate configurations are possible using EFAB® processes.

FIGS. 8-11 illustrate embodiments of embodiments of joining section 16 formed with an electro-forming process, such as electrodeposition, EFAB® process or a lithography process. In the embodiments of FIGS. 8-11, joining section 16 respectively includes first section 80, 90, 100, and 110 and second section 82, 92, 102, and 112. First and second sections 80, 90, 100, 110 and 82, 92, 102, 112 are formed with an electro-forming process, such as electrodeposition, EFAB® process or a lithography process.

In one embodiment illustrated in FIG. 8, first section 80 includes first and second plug portions 80a and 80b, and second section 82 is configured to receive first and second plug portions 80a and b. In the illustration, second section 82 is ghosted and first and second plug portions 80a and b are illustrated in dotted lines. As with first and second sections 80 and 82, first and second plug portions 80a and 80b can be formed with electro-forming processes, such as electrodeposition, EFAB® process or a lithography process. In one example, having features such as plug portions 80a and 80b formed within a receiving cavity of second section 82 can provide increased holding force between first and second section 80 and 82 when there is significant pulling or torque applied to proximal section 12 and distal section 14, which are respectively coupled to ends 16a and 16b.

In one embodiment illustrated in FIG. 9, first section 90 includes plug portion 90a, and second section 92 is configured to receive plug portion 90a. In the illustration, second section 92 is ghosted and plug portion 90a is illustrated in dotted lines. As with first and second sections 90 and 92, plug portion 90a can be formed with electro-forming processes, such as electrodeposition, EFAB® process or a lithography process. In one example, having a feature such as plug portion 90a formed within a receiving cavity of second section 92 can provide increased holding force between first and second section 90 and 92 when there is significant pulling or torque applied to proximal section 12 and distal section 14, which are respectively coupled to ends 16a and 16b.

In one embodiment illustrated in FIG. 10, first section 100 includes plug portion 100a, and second section 102 is configured to receive plug portion 100a. In the illustration, second section 102 is ghosted and plug portion 100a is illustrated in dotted lines. As with first and second sections 100 and 102, plug portion 100a can be formed with electro-forming processes, such as electrodeposition, EFAB® process or a lithography process. In one example, having a feature such as plug portion 100a formed within a receiving cavity of second section 102 can provide increased holding force between first and second section 100 and 102 when there is significant pulling or torque applied to proximal section 12 and distal section 14, which are respectively coupled to ends 16a and 16b.

In one embodiment illustrated in FIG. 11, first section 110 includes first and second plug portions 110a and 110b, and second section 112 is configured to receive first and second plug portions 110a and b. In the illustration, second section 112 is ghosted and first and second plug portions 110a and b are illustrated in dotted lines. As with first and second sections 110 and 112, first and second plug portions 110a and 110b can be formed with electro-forming processes, such as electrodeposition, EFAB® process or a lithography process. In one example, having features such as plug portions 110a and 110b formed within a receiving cavity of second section 112 can provide increased holding force between first and second section 110 and 112 when there is significant pulling or torque applied to proximal section 12 and distal section 14, which are respectively coupled to ends 16a and 16b. Use of these above-described processes, such as electrodeposition, three-dimensional printing, direct typing process, LIGA, lithography or stacking processes, enables features, such as joint 65, plug 70a, plug portions 80a and 80b, 90a, 100a, 110a and 110b to be produced even where the wire size is quite small. For example, even where the outer diameter of the wire is between 0.005 and about 0.02 inches, these processes allow for the feature to be produced in the joining section, thereby holding the first and second materials together.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A wire comprising:
a first wire section comprising a first material;
a second wire section comprising a second material different from the first material; and
a joining section that is separate from and adjacent to both the first and second wire sections, the joining section comprising a first end comprising a first joining section material and a second end comprising a second joining section material that is different from the first joining section material;
wherein the first end of the joining section is coupled to the first wire section defining a first interface, the first joining section material being compatible with the first material of the first wire section across the entire first interface, and wherein the second end of the joining section is coupled to the second wire section defining a second interface, the second joining section material being compatible with the second material of the second wire section across the entire second interface; and
the joining section comprising a feature configured hold the first joining section material to the second joining section material.

2. The wire of claim 1, wherein the feature comprises a joint between the first and second joining section materials that extends perpendicular relative to the first and second ends of the joining section.

3. The wire of claim 1, wherein the feature comprises a plug comprising the first joining section material that is configured within the second joining section material of the joining section.

4. The wire of claim 1, wherein the first material comprises one of stainless steel, nickel-chromium alloy, nickel-chromium-iron alloy, and cobalt alloy and wherein the second material comprises nickel-titanium.

5. The wire of claim 1, wherein the first joining section material of the first end of the joining section comprises the first material and the second joining section material of the second end of the joining section comprises the second material.

6. The wire of claim 1, wherein the joining section is produced via one of a group comprising electrodeposition, three-dimensional printing, direct typing process, LIGA, lithography and stacking processes.

7. The wire of claim 1, wherein materials of the joining section comprise a gradient of materials progressing from the first joining section material at the first end to the second joining section material at the second end.

8. The wire of claim 1, wherein the joining section is a cylindrical coupler separate from first and second wire sections to which each of the first and second sections are welded.

9. The wire of claim 1, wherein the first end of the joining section is welded to the first wire section and the second end of the joining section is welded to the second wire section.

10. The wire of claim 1, wherein the outer diameter of the wire is between 0.005 and about 0.02 inches.

11. A wire comprising:
a first wire section comprising a first material;
a second wire section comprising a second material different from the first material; and
a joining section that is separate from and adjacent to both the first and second wire sections, the joining section comprising a first end comprising a first joining section material and a second end comprising a second joining section material that is different from the first joining section material;
wherein the first end of the joining section is coupled to the first wire section and is characterized in that the first joining section material is entirely compatible with the first material of the first wire section throughout an entire area where the joining section and the first wire section are coupled; and
wherein the second end of the joining section is coupled to the second wire section and is characterized in that the second joining section material is entirely compatible with the second material of the second wire section throughout an entire area where the joining section and the second wire section are coupled.

12. The wire of claim 11, wherein the first material and the first joining section material are the same material and wherein the second material and the second joining section material are the same material.

* * * * *